United States Patent [19]

Grund et al.

[11] Patent Number: 4,855,465
[45] Date of Patent: Aug. 8, 1989

[54] PROCESS FOR THE TREATMENT OF ALIPHATIC EPOXIDES

[75] Inventors: Andreas Grund, Darmstadt; Guenter Prescher, Hanau; Georg Boehme; Willi Hofen, both of Rodenbach; Heinrich Petsch, Hanau, all of Fed. Rep. of Germany

[73] Assignee: Degussa Aktiengesellschaft, Frankfurt, Fed. Rep. of Germany

[21] Appl. No.: 166,784

[22] Filed: Mar. 2, 1988

Related U.S. Application Data

[63] Continuation of Ser. No. 890,573, Jul. 30, 1986, abandoned.

[30] Foreign Application Priority Data

Aug. 5, 1985 [DE] Fed. Rep. of Germany ....... 3528005

[51] Int. Cl.$^4$ ........................................... C07D 301/12
[52] U.S. Cl. ................................... 549/525; 549/526; 549/527; 549/528; 549/541
[58] Field of Search ............... 549/525, 541, 526, 527, 549/528

[56] References Cited

U.S. PATENT DOCUMENTS 3,030,336  4/1962  Greenspan et al. .................... 260/47
3,351,635  11/1967  Koller ................................. 549/529
4,059,619  11/1977  Prescher et al. ................. 260/502 R
4,101,570  7/1978  Krugër et al. .................. 260/502 R

FOREIGN PATENT DOCUMENTS 061393   9/1982  European Pat. Off. .
090239   3/1983  European Pat. Off. .
1203463  8/1963  Fed. Rep. of Germany .
1518227  7/1978  United Kingdom .
2019845  11/1979  United Kingdom .
2109797  6/1983  United Kingdom .

OTHER PUBLICATIONS

Hackh's Chemical Dictionary, p. 498, "Peracid".

Primary Examiner—Richard L. Raymond
Attorney, Agent, or Firm—Beveridge, DeGrandi & Weilacher

[57] ABSTRACT

Aliphatic epoxides of the formula:

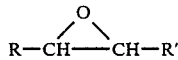

can be prepared in a technically efficient manner from the corresponding olefins by means of perpropionic acid in a benzene solution. The benzene solution can also be 1.5 weight percent of hydrogen peroxide, 1.5 weight percent of water and about 800 ppm of mineral acid.

11 Claims, 2 Drawing Sheets

PROCESS FOR THE TREATMENT OF ALIPHATIC EPOXIDES

This application is a continuation of application Ser. No. 06/890,573 filed July 30, 1986, now abandoned.

The present invention relates to a process for the preparation of aliphatic epoxides of the following formula:

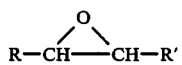

by epoxidation of olefins of the formula:

in which R represents an alkyl residue and R' represents an alkyl residue or hydrogen, with a percarboxylic acid in an organic solvent, as well as the processing of the reaction mixture thus formed.

Epoxides of the abovementioned structure are valuable intermediates, e.g., for the preparation of diols, as components of surface active substances, for the synthesis of a wide variety of organic intermediates, as well as for the polymer field.

The preparation of epoxides by reacting olefins with chlorine in an alkaline medium and subsequent treatment with bases has been known for a long time (Ullmann's Enzklopädie der technischen Chemie, 3rd ed., Vol. 10, page 565). The major disadvantage of this previously described process resides in the substantial amounts of environmentally damaging waste water, which necessarily results from this process. It is further known that ethylene can be epoxidized in high yields in the gas phase with molecular oxygen utilizing silver containing catalysts. This process is unsuitable for other olefins, however, because of its lack of selectivity.

Furthermore, olefins can be converted into corresponding epoxides by reaction with hydroperoxides, which can be obtained from hydrocarbons such as, for example, isobutane or ethylbenzene by oxidation with air in the presence of a catalyst containing vanadium molybdenum, or tungsten compounds (U.S. Pat. No. 3,351,635). This previously known method has the major drawback in addition to the need for separation of the catalyst system; the alcohol that is obtained in an equimolar amount from hydroperoxide as a coupled product, when it is not economically usable, can be recycled into hydroperoxide only with considerable technical expenditure.

The previously mentioned disadvantages can be partially avoided or prevented by means of the "Prileschajew reaction" (N. Prileschajew, Ber. Dtsch. Chem. Ges. 42, 4811 (1909)). This, in essence, is the reaction of an olefin with an organic percarboxylic acid. It is recognized that the use of, e.g. performic acid forms explosive mixtures at relatively high concentrations, and produces considerable quantities of waste water that requires careful disposal. The use of peracetic acid as well in an aqueous medium produces large quantities of undiluted acetic acid, which cannot be concentrated and recycled economically. If, as is often necessary because of product stability, the peracetic acid is buffered during the process with an alkali carbonate solution and/or neutralized after the reaction with alkali hydroxide solution, strongly saline waste water is produced with considerable impact on the environment.

Use of organic percarboxylic acids in an organic solvent is therefore presumed to be advantageous. Thus, the preparation of aliphatic 1,2-epoxides in the range of $C_9$-$C_{20}$ by reaction of their corresponding olefin with a solution of an organic per acid containing 3 to 4 carbon atoms is old in the art. Perbenzoic acid in benzene is preferred (German DE-OS No. 31 01 037 and European Patent Application EP-OS No. 056 932).

However, according to this known process, an excess of 50% to 500% of the olefin to be epoxidized is deemed necessary, and therefore this process cannot be considered as economically attractive. On the other hand, relatively high reactor volumes are necessary, and, on the other, the excess olefin must be separated from the reaction mixture at considerable expense and purified before being eventually returned to the epoxidation process.

It is recognized in the art that reaction mixtures obtained in this manner with per acids, because of their water and acid content, e.g., acetic acid, react very readily with the resulting epoxides to form by products such as glycols and glycol mono- and diesters (cf. German DE-AS No. 15 43 032). Therefore, epoxidation processes that employed performic or perpropionic acid, for example, appeared to be very difficult to carry out in an acid environment, because this resulted in cleavage of the oxirane ring (cf. German Patent DE-PS No. 29 16 834).

It is noted in this regard that a percarboxylic acid solution with a mineral acid content less than 50 ppm is claimed in German DE-OS No. 31 01 037 and in European Patent Application EP-OS No. 056 932, which describe the preparation of n-alkyloxiranes by means of perpropionic acid. According to the specification, the mineral acid content is preferably even less than 10 ppm.

Therefore, according to the above teachings of prior art, it was not expected that aliphatic olefins could be converted into their epoxides with perpropionic acid in a benzene solution, which contains up to 1.5 weight percent hydrogen peroxide, 1.5 weight percent of water, and 800 ppm of mineral acid, without appreciable formation of by products.

The invention has as its object the preparation of aliphatic epoxides using perpropionic acid with high yields and with the avoidance of interfering by product formation.

It has now been found that this object can be achieved, if an olefin of the formula:

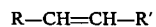

in which R represents an alkyl residue and R' represents an alkyl residue or hydrogen, is reacted with a solution of perpropionic acid in benzene at a molar ratio of 1:1 to 1:1.3, preferably 1:1.03 to 1:1.10, (olefin to perpropionic acid) at a temperature of 10° to 100° C.

R and R' can be alkyl residues with up to 28 C atoms, whereby R plus R' are equal to or greater than 8. It is preferred that R is $C_8$-$C_{28}$ and R' is H; i.e., alphaolefins, are preferred. Likewise, alpha, omega-diolefins can also be used, such as, for example, 1,9-decadiene. It is also possible to employ olefin cuts, e.g., in the range of $C_{20}$ to $C_{30}$, preferably of $C_{20}$ to $C_{26}$.

Novel and especially advantageous according to the process of the invention is the fact that both reactants can be employed in equimolar amounts or a very limited excess of per acid.

Perpropionic acid can be prepared, for example, according to a process disclosed in West German Patent DE-PS No. 25 19 289 by reacting aqueous hydrogen peroxide with propionic acid in the presence of sulfuric acid, then extracting the resulting perpropionic acid with benzene from the reaction mixture. The perpropionic acid in benzene solution obtained thereby can be purified still further to reduce the residual content of sulfuric acid, water, and hydrogen peroxide (cf. West German Patent DE-PS No. 25 19 290). However, a perpropionic solution is preferred that requires no further purification; in other words, the crude extract from the preparation of perpropionic acid can be used directly as such. This results in a considerably reduced technical expenditure.

Therefore, a perpropionic acid solution in benzene can be used that contains up to 1.5 weight percent of hydrogen peroxide, 1.5 weight percent of water, and up to 800 ppm of mineral acid.

According to the process of the present invention, the olefins which are a liquid at room temperature or reaction temperature are preferably used as such, but can be also diluted in a suitable solvent, whereby a wide range of concentrations can be freely selected.

The olefins which are solids under the abovementioned conditions can be employed as melts or dissolved in a suitable solvent, preferably benzene, whereby the concentration can likewise be selected freely over a wide range. Toluene, halogenated hydrocarbons, such as methylene chloride, chloroform, and carbon tetrachloride, are also suitable in addition to benzene; benzene is particularly preferred.

Preferably, the reaction occurs at temperatures of 20° to 70° C. The novel process can be run at various pressures; in general, standard pressure is used, but the process can also be run at excess or subatmospheric pressure.

The reaction can be run both as a batch process or as a continuous process in reactors suitable for this type of reaction. Suitable rectors include agitated kettles, agitated kettle cascades, and tubular or loop-type reactors, whereby the heat of the reaction can be removed in any manner, e.g, by evaporative cooling or by internal or external cooling equipment.

Glass, special steel, or enameled material are suitable fabrication materials for the reactors for carrying out the process embodying the invention.

The perpropionic acid is combined with the olefin or the solution thereof in a suitable solvent in any way desired. For example, both reactants can be introduced into the reactor together or in succession in any order of sequence. In a batch operating mode, the olefin is preferably introduced first and the per acid is metered in while the reaction temperature is monitored. However, the reaction can also be performed in reverse order, i.e., the per acid is charged first and the olefin is metered in with temperature monitoring. If the reaction is run continuously, both reactants can be fed into the reactor separately or together. If several series connected reactors are used, such as, for example, an agitated kettle cascade or a series of agitated kettles with a tubular reactor as the subsequent reactor, the addition of both the per acid and the olefin can be distributed over several reactors. Although benzene is the preferred solvent, toluene, chlorobenzene, or halogenated aliphatics such as methylene chloride, chloroform and carbon tetrachloride can be used also to dissolve the olefin.

No catalyst is required for the process of the present invention.

According to the process of the invention, a continuous mode of operation is very advantageous. According to this mode, the aliphatic olefin is charged with a solution of perpropionic acid in benzene at a molar ratio of 1:1 to 1:1.3 at the indicated temperatures of 10° to 100° C. to a reactor system. The system comprises a series of 1 to 4 ideally mixed reactors and a subsequent reactor. The residence time is adjusted so that the conversion, based on the amount of olefin double bond used, is at least 80 mole percent downstream of the ideally mixed reactor(s) and at least 95, preferably over 98, mole percent downstream of the subsequent reactor. Thereafter, the reaction mixture leaving the subsequent reactor is liberated in a combination of distillation and desorption steps from benzene, propionic acid, unreacted perpropionic acid, and other volatile components. This separation of the reaction mixture can be carried out according to one of the following embodiments, because the resulting epoxide is the component with the highest boiling point in the mixture.

The invention is further illustrated by the drawings, wherein.

The following is a detailed description of the invention including various embodiments thereof with reference to the accompanying drawings.

Embodiment 1 (Batch Process)

According to this embodiment, the individual components of the reaction mixture are removed in the order of their respective boiling points, individually or as a mixture by distillation or by distillation and desorption. In this process, the fractions of benzene, residues of perpropionic acid, propionic acid, and other readily volatile components are easily removed. The epoxide remains as the bottoms. If desired, the separated benzene and the propionic acid can be returned to the per acid synthesis after additional purification steps.

Figure 1:
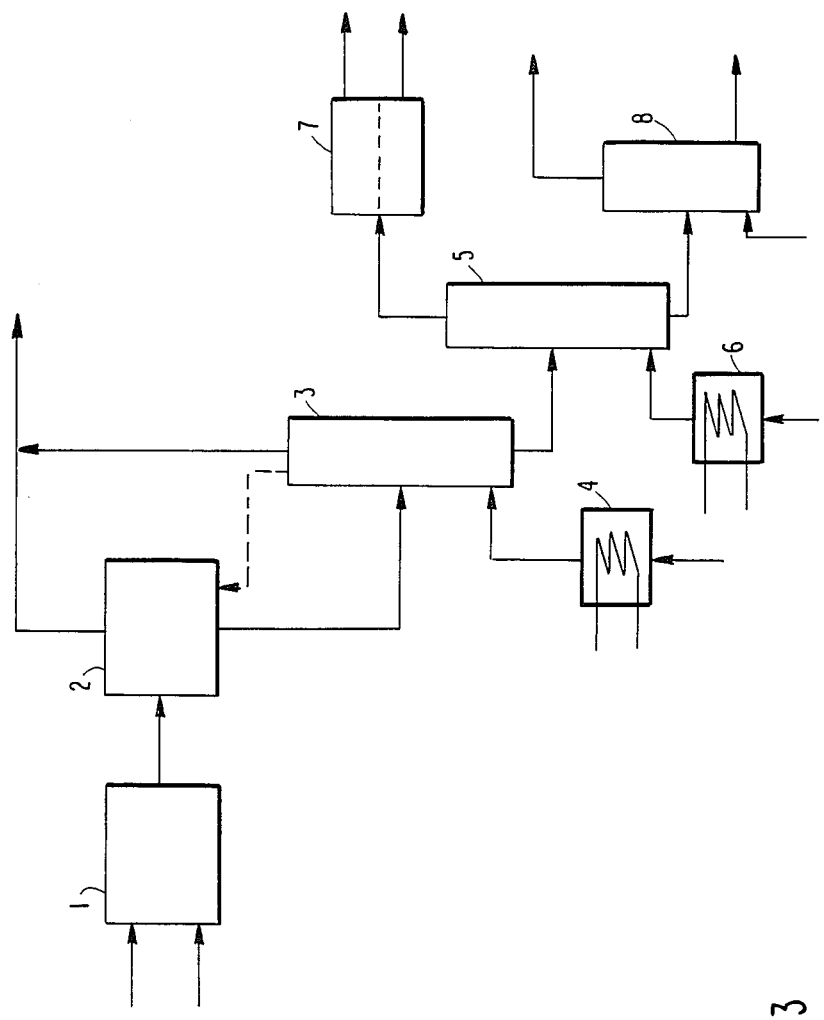
FIG. 1 is a flow diagram for a continuous process according to the invention.

Embodiment 2 (Continuous Process, FIG. 1)

According to this continuous variant of the process and as illustrated in FIG. 1, after the reaction mixture has left reaction unit 1, most of the benzene, propionic acid, and unreacted perpropionic acid are first removed in the one- or multistage distillation unit 2. Suitable for distillation devices are thin film, falling film, or circulation evaporators. Advantageously, distillation is effected at a reduced pressure of 0.5 to 600, preferably 10 to 300, mbar (temperature of the heating medium is 50° to 150° C.). Average residence times, based on the individual evaporation stages, are a maximum of 10 minutes, residence times of a maximum of 5 minutes being preferred.

According to the process of the invention, any amount of propionic acid remaining in the crude product is then removed by desorption at temperatures of the heating medium of 50° to 150° C. and a pressure of 0.5 to 600, preferably 10 to 300 mbar, in desorption unit 3 with benzene vapor that is generated in evaporator 4. The vapors from desorption unit 3 can either be conducted past distillation unit 2 or be passed therethrough.

After this step, any remaining traces of benzene are desorbed from the epoxide with steam from evaporator 6 in desorption unit 5 and/or with nitrogen or other inert gases in desorption unit 8. It is especially preferred to desorb first with steam, then with inert gases. The condensate from desorption unit 5 separates in phase separator 7 into an organic phase and water. The water is returned to evaporator 6, after enrichment, if necessary. The organic phase, which contains mostly benzene and propionic acid, is returned to perpropionic acid synthesis or to epoxidation after further processing, if necessary. Likewise, the streams of condensate consisting primarily of benzene and unreacted perpropionic and propionic acids and originating from distillation of desorption units 2 and 3, are returned, after further separation - cf. FIG. 3 - which will be described below; to per acid synthesis or to epoxidation.

In all examples, devices such as, for example, the falling film evaporator, Sambay evaporator, columns with built in packing or fill packing material, or similar means that enable proper mass transfer between gaseous and liquid states and are known to those skilled in the art are suitable as the desorption unit.

Figure 2:
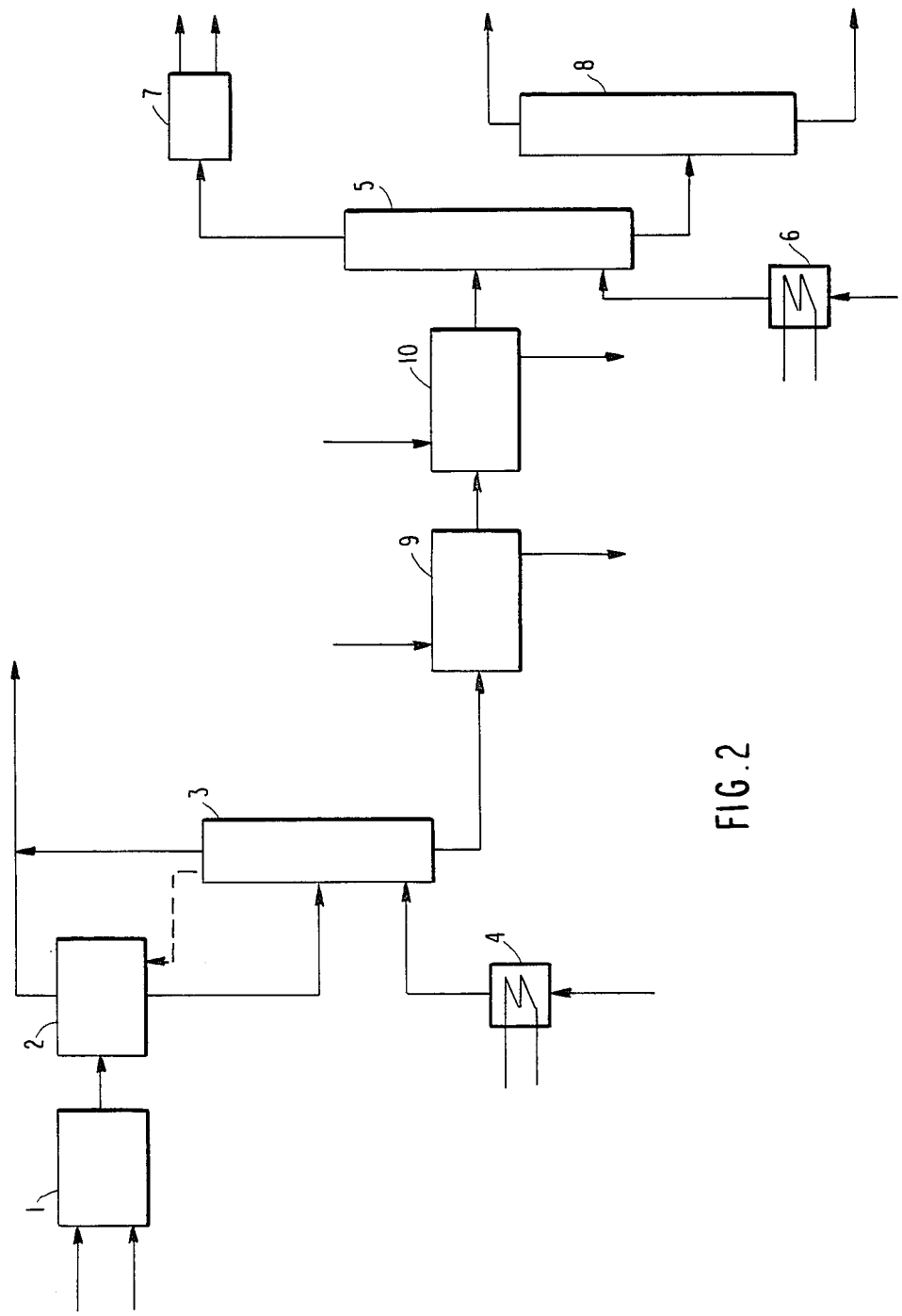
FIG. 2 is a flow diagram for a different continuous process according to the invention.

Embodiment 3 (Continuous Process, FIG. 2

According to the third embodiment to be used in a continuous manner, benzene, unreacted perpropionic acid, and propionic acid, as in Embodiment 2, are removed in the one- or multistage distillation unit 2. Then, the remaining propionic acid is desorbed with benzene vapor in desorption unit 3. To remove the remaining traces of propionic acid, the crude epoxide is now washed with aqueous alkalies in the extraction 9, and then with water in the one- or multistage extraction unit 10. Suitable devices for these steps are various types of extraction columns or mixer settler units as well. The method of operation and design of such apparatus are well known to workers in the art. Solutions of, for example, NaOH, KOH, $Na_2CO_3$, $K_2CO_3$, $NaHCO_3$, $KHCO_3$, $NH_3$, etc., are suitable as aqueous alkali solutions, the concentrations of which can be freely selected over a wide range. An NaOH solution with a concentration of 0.01 to 5 weight percent,, preferably 0.01 to 1.0 weight percent, is particularly preferred.

If mixer settler units are used for the water wash, the water can be supplied countercurrently, but each unit can also be operated with fresh water. Advantageously, a portion of the waste water from the mixer settler is used to prepare the alkali solution. The alkali and water washes can be carried out in a temperature range of 10° to 90° C.; temperatures between 30° to 70° C. are preferably. In the alkali wash, the weight ratio of the treated epoxide to alkali solution is 1:1 to 100:1 in the water wash, the ratio of epoxide flow rate to water flow rate is 1:1 to 100:1.

The water wash is followed by further progressing by desorption with steam and/or inert gas as described in Embodiment 2.

Figure 3:
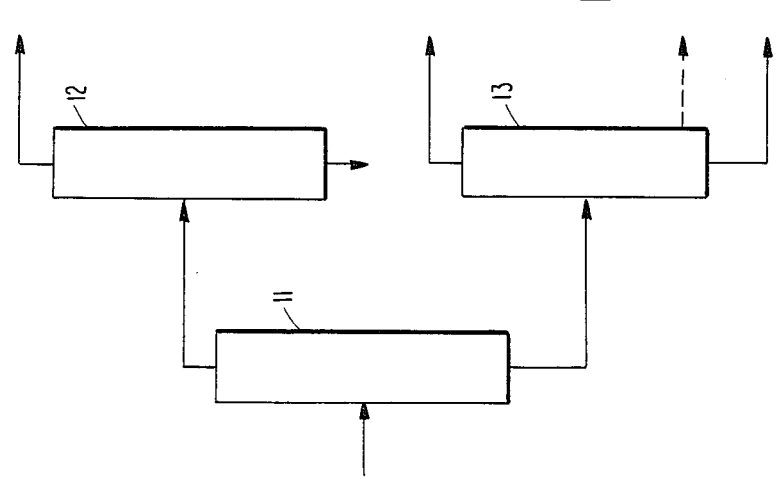
FIG. 3 is a flow diagram of a distillation system according to the invention.

In all embodiments of the invention resulting from a combination of distillation and desorption steps, condensates are obtained which are composed mainly of benzene, unreacted perpropionic acid, and other light boiling substances. According to the process of the invention, these materials are transferred to distillation unit 11 consisting of one or more columns (FIG. 3). This unit produces benzene as the overhead and in some cases other light boiling substances. In certain cases, the former is returned, after further distillation, to unit 12 for the preparation of perpropionic acid. A mixture of propionic acid, perpropionic acid, and benzene with benzene proportions of 5 to 35 weight percent referred to the bottoms mixture, accumulates in the bottom of distillation unit 11. This mixture is fed to another distillation unit 13, in which the total amount of added benzene and perpropionic acid with portions of propionic acid is drawn off at the top. In so doing, a concentration of perpropionic acid in the distillate of 25 weight percent is not exceeded. This overhead is returned to the process of preparing perpropionic acid or to the reaction of the olefin with perpropionic acid. Propionic acid is obtained as bottoms in column 13. After further processing such as by high purity distillation, the propionic acid is recycled to the preparation of perpropionic acid, after supplementing if necessary. It is of particular advantage to draw off the propionic acid obtained in unit 13 as a vapor above the bottoms and to condense it, thereby dispensing with one more purification step.

According to the invention, all distillation or desorption processing steps are preferably carried out at reduced pressure, e.g., 0.5 to 600 mbar. Columns in which benzene or propionic acid is obtained as overhead can likewise be run at standard pressure.

In the workup of the reaction mixture according to all variants, the epoxide is obtained as the high boiling component, namely as the bottoms. Depending on the requirements of the intended purpose or further processing, the epoxide can be employed directly or following another high purity distillation, which occurs preferably in vacuum.

The novel process offers a series of surprising advantages.

According to this process, it is possible via the so-called Prileschajew reaction to produce the above-mentioned epoxide on a commercial scale safely and with high yields. The product thus obtained is distinguished byits exceptional purity, high epoxide content, and light color.

The process described herein is economical, since all auxiliary agents are recycled. The process is by no means harmful to the environment, because only water is the waste product from the oxidation agent. Moreover, only small amounts of other light boiling substances, and distillation residues are obtained, which can be disposed of safely and without serious problems.

According to the invention, only short reaction times are necessary, which makes the commercial operation highly cost effective.

It is surprising and unforeseeable that the reaction of the abovementioned olefins with a crude perpropionic acid, which still contains mineral acid, water, and hydrogen peroxide in the concentrations mentioned above, can be carried out, and that side and secondary reactions are suppressed to the highest degree possible. Furthermore, it was unforeseeable that the reaction mixture thus obtained can be processed according to the invention by distillation or by distillation and desorption, without markedly reducing the epoxide content of the product.

The invention is further illustrated and described in the following examples.

EXAMPLE 1 (BATCH)

2700 g (6.6 moles) of perpropionic acid (22 weight %) in benzene was added over a 1 h period to 840 g (6.0 moles) of 1-decene with stirring and cooling to 850° C. Stirring was continued for 2 h at 60° C. The olefin conversion at this point was 98.4%. The clear, pale yellow solution thus obtained was passed through a thin film evaporator over a 2.5 period at 80° C. and a pressure of 100 mbar, during which about 347 g/h of benzene vapor was introduced countercurrently at the same time. The crude epoxide thus obtained was now passed through the thin film evaporator at 80° C./30 mbar; a weak nitrogen stream was passed countercurrently.

902 g of decene oxide with an epoxide content of 96.5% was obtained as the bottoms products.

EXAMPLE 2 (BATCH)

1718 g (4.2 moles) of perpropionic acid (22 weight %) in benzene was added over a 1.5 h period to 1008 g (4.0 moles) of 1 octadecene with stirring and cooling to 60° C. Stirring was continued for 3 h at 70° C. The olefin conversion at this point was 98.4%. The clear, pale yellow solution thus obtained was passed through a thin film evaporator over a 2.5 h period at 90° C. and a pressure of 100 mbar, during which about 230 g/h of benzene vapor was introduced countercurrently at the same time. The crude epoxide thus obtained was then passed through the thin film evaporator at 90° C./20 mbar; a weak nitrogen stream was passed countercurrently.

1057 g of octadecene oxide with an epoxide content of 95.5% was obtained as the bottoms.

EXAMPLE 3 (BATCH)

430 g (1.05 moles) of perpropionic acid (22 weight %) in benzene was added over a 45 minute priod to 361 g of a $C_{24}$-$C_{28}$ alpha-olefin mixture (average molecular weight was 360) with stirring and cooling to 55° C. Stirring was continued for 4 h at 70° C. The olefin conversion at this point was 97.8%. The clear, pale yellow solution thus obtained was passed through a thin film evaporator over a 60 minute period at 90° C. and a pressure of 100 mbar, during which about 315 g of benzene vapor was introduced countercurrently at the same time. The crude epoxide thus obtained was now passed through the thin film evaporator at 90° C./20 mbar; a weak nitrogen stream was passed countercurrently.

369 g of a solid epoxide mixture, which no longer showed any double bonds according to the $^1$H-NMR spectrum, was obtained as the bottoms product.

EXAMPLE 4 (BATCH)

1.43 moles of perpropionic acid in benzene (about 22 weight %) and 1.3 moles of 1-tetradecene (which corresponds to a molar ratio of per acid to olefin of 1.1:1) were charged hourly to the first agitated kettle of a reaction unit consisting of two agitated kettles each with a volume of 1500 ml and a subsequent reactor designed as a tubular reactor with a volume of 790 ml. The reaction temperature in reactor 1 was 50° C., in reactor 2 it was 51° C., and in the subsequent reactor it was 70° C. Conversions of olefin were 92.3% downstream of the agitated kettle cascade, and 98.4% downstream of the tubular reactor. According to Process Embodiment 2, benzene, perpropionic acid, and propionic acid were separated first in a Sambay evaporator with a surface area of 0.065 $m^2$ at a temperature of 83° C. and a pressure of 100 mbar. The residual propionic acid was desorbed in a second evaporator of the same type and same surface area at 86° C. and 100 mbar at a flow rate of 405 g/h of benzene vapor. All vapors from evaporator 2 were passed to evaporator 1 countercurrently to the product stream. Subsequently, the epoxide was treated in two desorption units, each consisting of a Sambay evaporator (surface area of 0.065 $m^2$) at 40 mbar with 31 g/h of steam and at 30 mbar with 14 g/h of nitrogen at temperatures of 95° C. 272.0 of epoxide with an epoxide content of 96.4% was obtained hourly as product.

EXAMPLE 5 (CONTINUOUS)

1.55 moles of perpropionic acid in benzene (about 22 weight %) and 1.48 moles of 1-octadecene (which corresponds to a molar ratio of per acid to olefin of 1 05:1) were charged hourly to the first agitated kettle of a reaction unit consisting of two agitated kettles each with a volume of 1500 ml and a subsequent reactor designed as a tubular reactor with a volume of 790 ml. The reaction temperature in reactor 1 was 60° C., in reactor 2 it was 60° C., and in the subsequent reactor it was 70° C. Conversions of olefin were 91.9% downstream of the agitated kettle cascade, and 98.6% downstream of the tubular reactor. According to Process Embodiment 2, benzene, perpropionic acid, and propionic acid were separated first in a Sambay evaporator with a surface area of 0.065 $m^2$ at a temperature of 80° C. and a pressure of 100 mbar. The residual propionic acid was desorbed in a second evaporator of the same type and same surface area at 80° C. and 100 mbar at a flow rate of 299 g/h of benzene vapor. The vapors from evaporator 2 were not passed through evaporator 1. Subsequently, the epoxide was treated in two desorption units, each consisting of a Sambay evaporator (surface area of 0.065 $m^2$) at 40 mbar with 30 g/h of steam and at 30 mbar with 14 g/h of nitrogen at temperature of 90° C. 390.8 g of epoxide with an epoxide content of 94.6% was obtained hourly as product.

EXAMPLE 6 (CONTINUOUS)

2.0 moles of perpropionic acid in benzene (about 22 weight %) and 1.9 moles of 1-dodecene (which corresponds to a molar ratio of per acid to olefin of 1.05:1) were charged hourly to the first agitated kettles each with a volume of 1500 ml and a subsequent reactor designed as a tubular reactor with a volume of 1900 ml. The reaction temperature in reactor 1 was 50° C., in reactor 2 it was 50° C., and in the subsequent reactor it was 60° C. Conversions of olefin were 92.7% downstream of the agitated kettle cascade, and 98.5% downstream of the tubular reactor. According to Process Embodiment 3, benzene, perpropionic acid, and propionic acid were separated first in a Sambay evaporator with a surface area of 0.065 $m^2$ at a temperature of 90° C. and a pressure of 100 mbar. The residual propionic acid was desorbed in a second evaporator of the same type and same surface area at 87° C. and 100 mbar at a flow rate of 320 g/h of benzene vapor. The crude epoxide thus obtained as bottoms was now washed in a mixer settler system with 0.1% sodium hydroxide solution (220 ml/h), then washed with water in a series of three mixer settler units (180 ml/h in each case). Subsequently, the epoxide was treated in two desorption units, each consisting of a Sambay evaporator (surface area of 0.065 $m^2$) at 18 mbar with 43 g/h of steam and at 21 mbar with 16 g/h of nitrogen at temperatures of 95° C. 340.1 g of epoxide with an epoxide content of 95.0% was obtained hourly as product.

The per acid in all tests was prepared according to West German DE-PS No. 25 19 289 and contained 0.57 weight % of hydrogen peroxide, 0.90 weight % of water and 620 ppm of sulfuric acid.

According to the process taught by the invention, the per acid content of solutions can vary from 10 to 30 weight percent.

Variations and modifications of the foregoing will be apparent to those skilled in the art and are intended to be encompassed by the claims appended hereto.

We claim:

1. A process for the preparation of an aliphatic epoxide of the following formula:

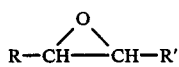

comprising reacting an olefin of the formula:

in which R represents an alkyl residue and R' represents an alkyl residue or hydrogen, with a solution of perpropionic acid at a concentration of 10–30% by weight in benzene at a molar ratio of 1:1 to 1:1.3 (olefin to perpropionic acid), wherein the aliphatic olefin with a solution of perpropionic acid in benzene at a molar ratio of 1:1 to 1:1.3 is charged to a reaction system consisting of a series of 1 to 4 ideally mixed reactors and a subsequent reactor, the reaction is run at a temperature of 10° to 100° C., whereby the residence time is adjusted so that the conversion, based on the olefin double bond used, is at least 80 mole percent downstream of the ideally mixed reactor(s) and over 98 mole percent downstream of the subsequent reactor, and separating the liberated propionic acid by a combination of distillation and desorption after the reaction to recover the desired product comprising removing benzene, propionic acid, small amounts of perpropionic acid, and other low boiling substances from the mixture emerging from the subsequent reactor in a combination of distillation and desorption steps, wherein the distillation and desorption steps are carried out at reduced pressure of 50° to 150° C. and with residence times of a maximum of 5 minutes, in the separated steps, wherein initially benzene and propionic acid, as well as small amounts of perpropionic acid, are removed for the most part by distillation, whereupon the amount of propionic acid remaining in the crude epoxide is further removed by desorption with benzene vapor, immediately thereafter driving off benzene and traces of propionic acid by desorption with steam and/or inert gases, and optionally following desorption with benzene vapor the crude epoxide is initially washed with aqueous alkalies, then washed with water, and only then the desorption with steam and/or inert gases is performed, wherein the perpropionic acid solution is the crude extract from the preparation of perpropionic acid which contains hydrogen peroxide, water and mineral acid and has a maximum content of 1.5 weight percent of hydrogen peroxide, 1.5 weight percent of water, and about 800 ppm of mineral acid.

2. The process according to claim 1, wherein the molar ratio is 1:1.03 to 1:1.10.

3. The process according to claim 1, wherein the reaction is run at a temperature of 20° to 70° C.

4. The process according to claim 1, wherein the olefins employed are those in which R represents $C_1$–$C_{28}$ alkyl residues and R' is hydrogen or a $C_1$–$C_{28}$ alkyl residue, and wherein the sum of R and R' is equal to or greater than 8.

5. The process according to claim 1, wherein R represents an alkyl residue with 8 to 28 carbon atoms and R' is hydrogen.

6. The process according to claim 1, wherein the mixture obtained by the combination of distillation and desorption steps and consisting of benzene, propionic acid, small amounts of perpropionic acid, and other remaining low boiling substances, is conducted to a distillation unit consisting of two or more distillation columns, and in which there is a unit (12) for the process of preparing perpropionic acid, and benzene, and any other low-boiling substances, is removed from the top in the first distillation step, and the former is returned to unit (12) for the process of preparing perpropionic acid after further distillation, and the total amount of prepropionic acid and propionic acid, as well as the portions of benzene at the bottom in amounts of 5 to 35 weight percent referred to the bottoms mixture, is removed, and the said bottom mixture is passed to a second distillation step in which the total amount of benzene and perpropionic acid contained therein with the portions of the propionic acid is removed at the top and in so doing a concentration of prepropionic acid in the overhead product of more than 25 percent is not exceeded, said overhead product being returned to the reaction of perpropionic acid with olefin, the propionic acid being drawn off as a vapor above the bottoms and condensed, is returned to unit (12) for the process of preparing perpropionic acid.

7. The process according to claim 1, wherein the starting olefin employed as an olefin mixture of $C_{20}$–$C_{30}$.

8. The process according to claim 7, hwerein the olefin mixture is $C_{20}$–$C_{26}$.

9. The process according to claim 1 which is continuous.

10. The process according to claim 1, wherein the mixture obtained by the combination of distillation and desorption steps and consisting of benzene, propionic acid, small amounts of perpropionic acid, and any other remaining low boiling substances, is conducted to a distillation unit consisting of two or more distillation columns, and in which there is a unit (12) for the process of preparing perpropionic acid, and benzene, and any other low boiling substances, is removed at the top in the first distillation step and the former is returned to unit (12) for the process of preparing perpropionic acid after further distillation, and the total amount of perpropionic acid and propionic acid, as well as the portions of benzene at the bottom in amounts of 5 to 35 weight percent referred to the bottom mixture, is removed, and the said bottom is passed to a second distillation step in which the total amount of the benzene and perpropionic acid contained therein with the portions of propionic acid is removed at the top and in so doing a concentration of perpropionic acid in the overhead product of more than 25 weight percent is not exceeded, said overhead product being returned to unit (12) for the process of preparing perpropionic acid, and the propionic acid being drawn off as a vapor above the bottoms and condensed, is returned to unit (12) for the process of preparing perpropionic acid.

11. The process as claimed in claim 1, wherein the molar ratio corresponds from about 1:1 to about 1.05 and the perpropionic acid solution contains about 22 weight percent perpropionic acid, about 0.57 weight percent hydrogen peroxide, about 0.90 weight percent water and about 620 ppm sulfuric acid as mineral acid.

* * * * *